(12) United States Patent
Li et al.

(10) Patent No.: US 6,770,790 B1
(45) Date of Patent: Aug. 3, 2004

(54) PURIFICATION OF TERTIARY BUTYL ALCOHOL

(75) Inventors: Xiangmin Li, West Chester, PA (US); Lawrence M. Candela, Havertown, PA (US); Yuan-Zhang Han, West Chester, PA (US); Andrew P. Kahn, Eagleville, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/688,410

(22) Filed: Oct. 17, 2003

(51) Int. Cl.[7] .................. C07C 27/34; C07C 29/76; C07C 27/26; C07C 29/74; C07C 29/88
(52) U.S. Cl. .................. 568/917; 568/913; 568/914; 568/915; 568/916; 568/918
(58) Field of Search .................. 568/917, 913, 568/914, 915, 916, 918

(56) References Cited

U.S. PATENT DOCUMENTS

| 4,239,926 A | 12/1980 | Grane et al. ............... 568/910 |
| 4,543,432 A | 9/1985 | Shih et al. ................. 568/917 |
| 6,417,412 B1 | 7/2002 | Kahn et al. ................ 568/917 |

*Primary Examiner*—Elvis O. Price
(74) *Attorney, Agent, or Firm*—Kevin M. Carroll

(57) ABSTRACT

The invention is a method to purify tertiary butyl alcohol by contact with at least two solid adsorbents comprising aluminum oxide and a large pore zeolite such as zeolite X. The purification method successfully improves product quality and reduces the amount of impurities in the tertiary butyl alcohol.

14 Claims, No Drawings

US 6,770,790 B1

PURIFICATION OF TERTIARY BUTYL ALCOHOL

FIELD OF THE INVENTION

This invention relates to the purification of tertiary butyl alcohol by contacting the impure tertiary butyl alcohol with at least two solid adsorbents comprising aluminum oxide and a large pore zeolite such as zeolite X. The process is especially useful for the separation of minor amounts of close boiling oxygenated impurities from the tertiary butyl alcohol.

BACKGROUND OF THE INVENTION

Generally tertiary butyl alcohol as produced by oxidation processes such as the Oxirane Process contains small but significant amounts of impurities is including water, isopropanol, acetone, methyl ethyl ketone, isobutanol, formate esters, secondary butyl alcohol and the like. In certain applications, the presence of such impurities causes problems with respect to the desired use. For example, "high purity" tertiary butyl alcohol is needed as a reagent for the synthesis of specialty products such as pharmaceuticals and agrichemicals, as a stabilizer of chlorinated hydrocarbons, in addition to other applications. It is thus desirable to provide a process by which the impurities can be conveniently separated from impure tertiary butyl alcohol to produce "high purity" tertiary butyl alcohol.

It is known that the close boiling oxygenated impurities can be separated to a significant degree from tertiary butyl alcohol by an elaborate and extensive distillation procedure. For example, see U.S. Pat. No. 4,239,926. However, such procedures are costly and time-consuming, involving substantial capital investments and utilities expenses.

Further research has focused on developing less costly or time-consuming purification processes. For instance, U.S. Pat. No. 4,543,432 shows the separation of isopropanol from a tertiary butyl alcohol process stream by absorption using an asymmetric carbonaceous absorbent such as Ambersorb® XE-347. Data are presented in Table 11 giving the equilibrium capacity of isopropanol on various adsorbents for a synthetic solution of isopropanol in tertiary butanol. Data for Type 5A and 13X molecular sieves indicate that Type 5A has a slightly higher equilibrium capacity than Type 13X. Additional data relative to Type 5A are given in Table IV. In addition, U.S. Pat. No. 6,417,412 teaches the purification of a tertiary butyl alcohol process stream by contact with a large pore zeolite in the sodium form (such as 13X).

In sum, new processes for the purification of tertiary butyl alcohol are needed. It is desirable to develop a simplified procedure whereby tertiary butyl alcohol process streams can be conveniently treated to separate close boiling impurities by a relatively simple and straightforward procedure.

SUMMARY OF THE INVENTION

The invention is a method of purifying tertiary butyl alcohol containing minor amounts of impurities. The method comprises contacting the tertiary butyl alcohol with at least two solid adsorbents comprising aluminum oxide and a large pore zeolite such as zeolite X or Zeolite Y. As a result of this contact, impurities are retained on the zeolite and alumina and are thus removed or separated from the tertiary butyl alcohol; product tertiary butyl alcohol reduced in the content of contaminating impurities is readily recovered. It is generally advantageous to operate with a plurality of contact zones since the contact material must be regenerated from time to time as it loses its effectiveness for impurities removal over extended use. With a plurality of treatment zones, tertiary butyl alcohol can be treated in one zone while a separate zone is being regenerated.

DETAILED DESCRIPTION OF THE INVENTION

Tertiary butyl alcohol as produced commercially, for example by the Oxirane Process, contains small but significant amounts of impurities. For example, the total amount of impurities contained in a tertiary butyl alcohol product stream typically are in the range of approximately 0.1 to about 3 weight percent of the tertiary butyl alcohol product stream. Illustrative of such impurities are water, isopropanol, acetone, methyl ethyl ketone, isobutanol, formate esters, and secondary butyl alcohol. The tertiary butyl alcohol stream to be treated illustratively comprises by weight about 10 ppm to 2% of each of the above impurities, usually about 20 ppm to 1% of each. Other materials that can readily be separated as by distillation such as methanol and methyl tertiary butyl ether may also be present.

In order to reduce the level of impurities in the tertiary butyl alcohol feed stream, the tertiary butyl alcohol is contacted in the liquid phase with at least two solid adsorbents. The adsorbents useful in the invention are aluminum oxide and a large pore zeolite. In accordance with the present invention, the impure tertiary butyl alcohol in the liquid phase is contacted with two adsorbents whereby impurities are retained on the two adsorbents and a liquid product tertiary butyl alcohol reduced in impurities content is conveniently separated.

The aluminum oxide adsorbent used in the practice of the invention is a solid material that contains a major proportion of alumina (aluminum oxide). Amorphous (i.e., non-crystalline) aluminum oxides are particularly preferred for use. In general, suitable aluminum oxides are further characterized by having a relatively large surface area in relation to their mass. The term used herein and one normally used in the art to express the relationship of surface area to mass is "specific surface area". The inorganic aluminum oxides for purpose of this invention have a specific surface area of at least 0.5 m$^2$/g, and preferably the average specific surface area is from 1 m$^2$/g to 1000 m$^2$/g, and most preferably from about 50 m$^2$/g to 500 m$^2$/g. Preferred inorganic aluminum oxides include various forms of alumina including α-alumina, γ-alumina, activated aluminas, and basic aluminas. Basic alumina as used herein refers to alumina having a surface area of 50–500 m$^2$/g which has been impregnated with a basic solution having a pH of at least 9 and dried. The basic solution may suitably be a solution of an alkali metal or ammonium compound such as one selected from hydroxides, carbonates, bicarbonates, phosphates, and organic acid salts. Suitable basic compounds that may be employed include sodium, potassium or ammonium carbonate, hydroxide, bicarbonate, nitrate, formate, acetate, benzoate or citrate. Activated aluminas are partially hydroxylated aluminum oxide whose chemical compositions can be represented by the formula $Al_2O_{(3-x)}(OH)_{2x}$, where x ranges from about 0 to 0.8. Activated aluminas are particularly preferred.

In addition to the aluminum oxide, tertiary butyl alcohol is also contacted with a large pore zeolite. The large pore zeolites are useful for the removal of essentially all of the impurities as above described, which are normally associated with tertiary butyl alcohol process streams. The large pore zeolite used in the present invention are crystalline aluminosilicates having a pore size greater than about 6 Angstroms and preferably having an average pore size from about 6 Angstroms to about 15 Angstroms. Particularly preferred are zeolite X and zeolite Y. Preferably, the large pore zeolite is in the alkali metal (e.g., sodium) form rather than the acid form in order to provide effective impurities removal. Large pore zeolites are well known in the art.

The adsorptive contact is conveniently carried out at moderate temperatures, although temperature is not especially critical. Suitable temperatures are in the range of about 25° C. to 150° C., preferably 25° C. to 60° C. The freeze point of the purified tertiary butyl alcohol is about 25° C. In general, higher adsorption temperature reduces adsorption capacity. Therefore, to maximize adsorption capacity of the adsorbents, the preferred adsorption temperature is within the range of from about 25° C. to 40° C. Flow rates of about is 0.005 to 50 volumes of tertiary butyl alcohol per volume of adsorbent per hour, preferably 0.02–5 are preferred. In general, slower feed flow rate gives less product impurity at a given bed-volume. Therefore, flow rate can be optimized depending on the volume of adsorbent utilized in the process.

The contact solids retain the impurities adsorbed thereon and purified tertiary butyl alcohol can be separated. Initially, there can be substantially complete removal of the impurities and the recovered tertiary butyl alcohol is of exceptional purity. Over the course of time the contact solids gradually become less effective for the removal of these components. In accordance with the present invention at a predetermined time when the separation efficiency has fallen below a desired point, the solid contact materials are effectively regenerated, as by contact with a heated vapor stream such as nitrogen or air at a temperature of at least 200° C. or by wash with a solvent such as methanol, acetone or water. It is advantageous to employ a plurality of parallel contact zones such that while one zone is being regenerated the feed is passed through a zone containing fresh or regenerated contact material so that optimum impurities removal can be achieved.

The large pore zeolite and aluminum oxide adsorbents may be mixed together or layered in a single adsorbent contact bed. Separate beds of large pore zeolite and aluminum oxide may also be employed. It is generally preferred to employ more than one adsorbent contact bed so that a depleted bed can be regenerated while a fresh bed is used. While the order in which the various adsorbent beds are used is not critical, it is preferred to utilize the alumina bed prior to the large pore zeolite bed.

In addition to the large pore zeolite and aluminum oxide, a molecular sieve may optionally be utilized to remove any excess water from the tertiary butyl alcohol. The molecular sieves useful in the invention are crystalline aluminosilicates having an average pore size of about 3 to about 5 Angstroms. Molecular sieves in the alkali metal form are preferred, such as molecular sieve 3A, 4A, or 5A. Molecular sieve 4A is particularly preferred. The molecular sieve may be regenerated according to the same procedures as for the aluminum oxide and the large pore zeolite. Thus, the molecular sieve may be regenerated by contact with a heated vapor stream such as nitrogen or air at a temperature of at least 200° or by wash with a solvent such as methanol or acetone.

The molecular sieve may be mixed together in a single adsorbent contact bed with the large pore zeolite and aluminum oxide adsorbents. A separate bed of molecular sieve may also be employed. While the order in which the various adsorbent beds are used is not critical, it is preferred to utilize the molecular sieve bed last as a finishing drying step.

The following examples merely illustrate the invention. Those skilled in the art will recognize many variations that are within the spirit of the invention and scope of the claims.

COMPARATIVE EXAMPLE 1: ADSORPTION RUN WITH ALUMINA

A stainless steel tube (1 in.×6 ft.) is packed with Selexsorb CD Alumina (a product of Alcoa). The tube is placed in an electric furnace and the temperature is controlled to 28° C. The feed of tertiary butyl alcohol (TBA) is passed upflow through the bed and samples are collected hourly for analysis by gas chromatography. Table 1 lists the weight and volume of adsorbent and the space velocity (LHSV) used for the adsorption run. Table 2 lists the product composition after purification.

COMPARATIVE EXAMPLE 2: ADSORPTION RUN WITH ZEOLITE 13X

Comparative Example 2 is run according to the procedure of Comparative Example 1 using large pore zeolite 13XHP (a product of UOP). Experimental conditions and results are listed in Tables 1 and 2.

EXAMPLE 3: ADSORPTION RUN WITH ALUMINA AND ZEOLITE 13X

Example 3 is run according to the procedure of Comparative Example 1 using two adsorbents, aluminum oxide (Selexsorb CD from Alcoa) followed by the large pore zeolite (13XHP from UOP). Experimental conditions and results are listed in Tables 1 and 2.

EXAMPLE 4: ADSORPTION RUN WITH ALUMINA, ZEOLITE 13X, AND MOLECULAR SIEVE

Example 4 is run according to the procedure of Comparative Example 1 using three adsorbents, aluminum oxide (Selexsorb CD from Alcoa), followed by the large pore zeolite (13XHP from UOP), followed by molecular sieve (4A from UOP). Experimental conditions and results are listed in Tables 1 and 2.

The adsorption results show that purification of tert-butyl alcohol is significantly improved when using at least two adsorbents comprising aluminum oxide and a large pore zeolite. Both adsorbents are very effective in removing impurities like sec-butyl alcohol, methanol, acetone, isopropanol, MEK, isobutanol, isobutyl formate, and water. However, without using aluminum oxide, tert-butyl formate break-through occurs rather early and limits the adsorption capacity.

Results also show that the purity of tert-butyl alcohol is further improved by contacting a molecular sieve at the end to reduce the water content of the product The combination of alumina, large pore zeolite, and molecular sieve purifies tertiary butyl alcohol to over 99.9%.

EXAMPLE 5: ADSORPTION OF FORMATES BY VARIOUS ALUMINA

Various types of alumina are tested and all are found to be effective in removing tert-butyl formate and isobutyl formate from the tertiary butyl alcohol feed. Alumina samples tested include F-200 (an activated alumina in size 7×14 Tyler mesh, product of Alcoa), DD-2 (an activated alumina in size 8×14, product of Alcoa), Selexsorb CDO-200 (an activated alumina in size 8×14 with high Lewis acidity, product of Alcoa), Selexsorb CDX (an activated alumina in size 7×14 Tyler mesh, product of Alcoa), Selexsorb CD (an activated alumina in size 7×14 Tyler mesh, product of Alcoa), and basic alumina (150 mesh, from Aldrich).

To test the various alumina, a 1 cm ID glass column is packed with different alumina, an unpurified TBA feed is then passed through the bed at a LHSV of approximately 0.22–0.29 hr$^{-1}$, and product is collected. Table 3 shows the adsorption results.

TABLE 1

Adsorption Run Data

| Run # | Adsorbent(s) | Adsorbent Amount (g) | Adsorbent Volume (cc) | LHSV (h$^{-1}$) |
|---|---|---|---|---|
| 1* | Selexsorb CD only | 488.3 | 700 | 0.06 |
| 2* | 13XHP only | 403.9 | 600 | 0.17 |
| 3 | Selexsorb CD, followed by 13XHP | 241.9 gm Selexsorb CD, 233.2 gm 13XHP | 340 cc Selexsorb CD, 350 cc 13XHP | 0.06 |
| 4 | Selexsorb CD, followed by 13XHP, followed by 4A | 201.5 gm Selexsorb CD, 197 gm 13XHP, 47 gm 4A | 300 cc Selexsorb CD, 300 cc 13XHP, 40 cc 4A | 0.07 |

*Comparative Example

TABLE 2

Adsorption Results

Wt. % of TBA Components

| TBA Components | Unpurified | 1* @ 0.6 Bed-volume (wt. %) | 2* @ 0.5 Bed-Volume (wt. %) | 3* @ 0.77 Bed-Volume (wt. %) | 4* @ 1.04 Bed-Volume (wt. %) |
|---|---|---|---|---|---|
| tert-butyl alcohol | 98.3156 | 99.7972 | 99.6682 | 99.8346 | 99.9427 |
| isobutene | | 0.0459 | 0.0341 | 0.0354 | 0.0383 |
| sec-butyl alcohol | 0.0300 | 0.0116 | 0.0126 | — | — |
| methanol | 0.0205 | — | — | — | — |
| acetone | 0.4710 | — | — | — | — |
| isopropanol | 0.1906 | 0.0357 | 0.0095 | — | — |
| Methyl ethyl ketone | 0.0969 | — | — | — | — |
| Tert-butyl formate | 0.4424 | 0.0066 | 0.2127 | — | — |
| Isobutanol | 0.1030 | 0.0290 | 0.0166 | — | — |
| Isobutyl formate | 0.1300 | | 0.0243 | — | — |
| water | 0.2000 | 0.0740 | 0.0220 | 0.1300 | 0.0190 |

*Comparative Example

TABLE 3

Results of Formate Removal by Various Alumina

| Adsorbent | Adsorbent Amount (gm) | LHSV (hr$^{-1}$) | Bed-Volumes | % tert-butyl formate Removal | % iso-butyl formate Removal |
|---|---|---|---|---|---|
| F-200 | 69.46 | 0.22 | 0.71 | 74.9 | 100 |
| | | | 0.93 | 73.2 | 100 |
| DD-2 | 52.41 | 0.25 | 0.74 | 72.6 | 100 |
| Selexsorb CDO-200 | 60.5 | 0.22 | 0.44 | 74.8 | 100 |
| Selexsorb CDX | 64.06 | 0.29 | 0.58 | 92.8 | 100 |
| | | | 0.87 | 77.9 | 100 |
| Selexsorb CD | 61.13 | 0.25 | 0.68 | 100 | 100 |
| | | | 0.92 | 86.8 | 100 |
| Basic Alumina powder | 60 | 0.22 | 1 | 100 | 100 |

We claim:

1. A method of treating tertiary butyl alcohol containing a minor amount of impurities which comprises contacting the tertiary butyl alcohol in the liquid phase with aluminum oxide and a large pore zeolite, and recovering a tertiary butyl alcohol product stream reduced in content of the impurities.

2. The method of claim 1 wherein the large pore zeolite has an average pore size from about 6 Angstroms to about 15 Angstroms.

3. The method of claim 1 wherein the large pore zeolite is zeolite X.

4. The method of claim 1 wherein the large pore zeolite is zeolite Y.

5. The method of claim 1 wherein the large pore zeolite is in the sodium form.

6. The method of claim 1 wherein the aluminum oxide is selected from the group consisting of α-alumina, γ-alumina, activated alumina, and basic alumina.

7. The method of claim 6 wherein the aluminum oxide is activated alumina.

8. The method of claim 1 wherein the aluminum oxide has a surface area in the range of from about 50 to about 500 m$^2$/g.

9. The method of claim 1 wherein the tertiary butyl alcohol is contacted with an additional adsorbent comprising a molecular sieve having an average pore size of about 3 to about 5 Angstroms.

10. The method of claim 9 wherein the molecular sieve is selected from the group consisting of 3A, 4A, and 5A.

11. The method of claim 9 wherein the molecular sieve is 4A.

12. A method of treating tertiary butyl alcohol containing impurities which comprises contacting the tertiary butyl alcohol with activated alumina, a large pore zeolite selected from the group consisting of zeolite Y and zeolite X, and a molecular sieve selected from the group consisting of 3A, 4A, and 5A, and recovering a tertiary butyl alcohol product stream reduced in content of the impurities.

13. The method of claim 12 wherein the large pore zeolite is in the sodium form.

14. The method of claim 12 wherein the molecular sieve is 4A.

* * * * *